(12) United States Patent
Charbit et al.

(10) Patent No.: US 7,652,034 B2
(45) Date of Patent: *Jan. 26, 2010

(54) ENANTIOMER (−) OF TENATOPRAZOLE AND THE THERAPEUTIC USE THEREOF

(75) Inventors: Suzy Charbit, Creteil (FR); Avraham Cohen, Tel Aviv (IL); Herve Ficheux, Nogent-sur-Marne (FR); Michel Homerin, Courcouronnes (FR); Francois Schutze, Saint-Non-la-Breteche (FR); Alain Taccoen, Le Chesnay (FR)

(73) Assignee: Sidem Pharma, Luxembourg (LU)

( * ) Notice: Subject to any disclaimer, the term of this patent is extended or adjusted under 35 U.S.C. 154(b) by 703 days.

This patent is subject to a terminal disclaimer.

(21) Appl. No.: 11/344,212

(22) Filed: Feb. 1, 2006

(65) Prior Publication Data

US 2006/0194832 A1    Aug. 31, 2006

Related U.S. Application Data

(62) Division of application No. 10/507,485, filed on Sep. 13, 2004, now Pat. No. 7,034,038.

(51) Int. Cl.
    *A61K 31/48*    (2006.01)
(52) U.S. Cl. .................................... 514/303; 546/118
(58) Field of Classification Search ................ 546/118; 514/303
    See application file for complete search history.

(56) References Cited

U.S. PATENT DOCUMENTS

| 5,948,789 | A | 9/1999 | Larsson et al. |
| 6,706,737 | B2 | 3/2004 | Whittle et al. |
| 7,034,038 | B2 * | 4/2006 | Cohen et al. ................. 514/303 |
| 2006/0241136 | A1 | 10/2006 | Schutze et al. |
| 2006/0287284 | A1 | 12/2006 | Schutze et al. |
| 2007/0066659 | A1 | 3/2007 | Schutze et al. |

FOREIGN PATENT DOCUMENTS

| EP | 0005129 | 10/1979 |
| EP | 0103553 | 3/1984 |
| EP | 0254588 | 1/1988 |
| WO | WO 94/27988 A1 | 12/1994 |
| WO | WO 01/28558 A1 | 4/2001 |

OTHER PUBLICATIONS

International Search Report issued in Application No. PCT/FR03/03746, dated May 19, 2004.
Jedediah Bateman et al., "Comparison of Pharmacokinetic Properties of Omeprazole and Esomeprazole", Pharmaceutics 1 (PSCI 423), Apr. 4, 2002.
"Esomeprazole—Proton Pump Inhibitors Revisited", RGH Pharmacy E-Bulletin, vol. 10 (7): Jun. 16, 2003.
Kakinoki, abstract only, CA 131:208915, Methods and Findings in Experimental and Clinical Pharmacology, 21(3):179-187 (1999).
Uchiyama, abstract only, CA 131:139269, Methods and Findings in Experimental and Clinical Pharmacology, 21(2):115-122 (1999).
Uchiyama, abstract only, CA 131:125259, abstract of J of Pharmacy and Pharmacology, 51(4):457-464 (1999).
U.S. Appl. No. 10/561,844 "Monohydrated Sodium Salt of S-Tenatoprazole and the Use Thereof in Therapy", filed Dec. 22, 2005.

* cited by examiner

*Primary Examiner*—D. Margaret Seaman
(74) *Attorney, Agent, or Firm*—Crowell & Moring

(57) ABSTRACT

The invention relates to enantiomer (−) of tentoprazole. The inventive enantiomer (−) of tenatoprazole, or (−)-5-methoxy-2-[[(4-methoxy-3,5-dimethyl-2-pyridyl)methyl]sulfinyl]imidazol[4,5-b]pyridine exhibits improved pharmacokinetic properties which make it possible to use a once a day posology of a drug for relevant indications. The enantiomer (−) of tenatoprazole can be used for treating digestive pathologies.

10 Claims, No Drawings

ENANTIOMER (-) OF TENATOPRAZOLE AND THE THERAPEUTIC USE THEREOF

This application is a divisional of U.S. patent application Ser. No. 10/507,485, filed Sep. 13, 2004, now U.S. Pat. No. 7,034,038 now allowed, the contents of which are incorporated herein by reference in their entirety.

FIELD OF THE INVENTION

The present invention concerns tenatoprazole, and more particularly an enantiomer of tenatoprazole, and specifically a method for its preparation and use in human or veterinary therapeutics.

BACKGROUND OF THE INVENTION

Tenatoprazole, or 5-methoxy-2-[[(4-methoxy-3,5-dimethyl-2-pyridyl)methyl]sulfinyl]imidazo[4,5-b]pyridine, is described in Patent No. EP 254.588. It belongs to the group of drugs classified under the name of "proton pump inhibitors" (PPIs), which inhibit the secretion of gastric acid and are useful for the treatment of gastric and duodenal peptic ulcers. Because of its relatively long elimination half-life, tenatoprazole can also be used for the treatment of conditions such as gastro-oesophageal reflux, digestive bleeding and dyspepsia, as described in the French patent application No. FR 02.13113.

The first known derivative of this series of PPIs was omeprazole, described in Patent No. EP 005.129, which has the property to inhibit the secretion of gastric acid and is widely employed as an anti-ulcer in human therapeutics.

In addition to omeprazole, other PPIs are now well known and particular mention can be made of rabeprazole, pantoprazole and lansoprazole, which all exhibit structural analogy and belong to the group of pyridinyl-methyl-sulfinyl-benzimidazoles. These compounds are sulfoxides which have an asymmetry at the level of the sulphur atom, and therefore generally take the form of a mixture (racemic mixture or racemate) of two enantiomers.

Different formulations have been proposed in order to improve the properties or the activity of PPIs. In the case of omeprazole, for example, the PCT application WO 01.28558 describes a stable liquid formulation obtained by forming the sodium or potassium salts in situ in solution in polyethylene glycol, by action of a hydroxide on omeprazole. The medicinal product thus formulated can be used in the usual indications of PPIs.

Like omeprazole and other sulfoxides with similar structure, tenatoprazole has an asymmetric structure and may therefore exist in the form of a racemic mixture and in the form of two enantiomers with configurations "R" and "S", or (+) and (-), respectively.

Recent studies have shown that unexpectedly and unlike all the other PPIs (such as, for example, omeprazole or lansoprazole), tenatoprazole possesses a remarkably long duration of action which is the result of a longer half-life in plasma (approximately seven times longer). Indeed, clinical data have shown that tenatoprazole induces a degree of symptom relief and healing of gastric lesions which is superior to those achieved by other PPIs, and which allows for its effective use in the treatment of diseases and conditions such as, for example, atypical and oesophageal symptoms of gastro-oesophageal reflux, digestive bleeding and dyspepsia.

Studies conducted by the applicant have unexpectedly shown that the (+) and (-) enantiomers of tenatoprazole contribute differently to the properties of tenatoprazole and exhibit significantly different pharmacokinetic properties. Thus, it is possible to isolate these enantiomers and prepare medicinal products with different pharmacokinetic profiles and specific activities. It then becomes possible to use each enantiomer more effectively for the treatment of specific diseases and conditions.

SUMMARY OF THE INVENTION

The present invention concerns the use of the (-) enantiomer of tenatoprazole in human or veterinary therapeutics.

One purpose of the present invention is the preparation of a pharmaceutical composition comprising the (-) enantiomer of tenatoprazole in combination with one or more pharmaceutically acceptable excipients and substrates.

The present invention also relates to a pharmaceutical composition comprising the (-) enantiomer of tenatoprazole in combination with one or more antibiotics.

A further object of the present invention is the use of the (-) enantiomer of tenatoprazole in the manufacture of a medicinal product to treat digestive diseases and conditions where the inhibition of acid secretion must be effective and prolonged to treat, for example, the symptoms and lesions of gastro-oesophageal reflux, or digestive bleeding refractory to other PPIs, and especially treat these diseases and conditions in patients receiving multiple drug therapy.

A further object of the present invention is the use of the (-) enantiomer of tenatoprazole in the manufacture of a drug with a significantly improved onset of healing as well as an increase in the rate of normalization of histological changes of the gastric lesions in animals or humans, which result in a sharp decrease in the relapse of oesophagitis, and thus for the prevention or the treatment of the relapse of oesophagitis.

The present invention also concerns the use of the (-) enantiomer of tenatoprazole in the manufacture of a medicinal product with improved pharmacokinetic properties that would allow taking a single dose of medication per day in relevant indications, and particularly in the eradication of *Helicobacter pylori* during the treatment of duodenal ulcer, condition which usually requires two doses (morning and evening) of other PPIs.

The (-) enantiomer of tenatoprazole can be used in the form of a salt, including an alkaline or earth-alkaline metal salt and, for example, in the form of a sodium, potassium, lithium, magnesium or calcium salt. These salts can be obtained from the (-) enantiomer of tenatoprazole that has previously been isolated by salification according to the standard method of the technique, for example by the action of basic mineral reagents comprising alkaline or earth-alkaline counter-ions.

DETAILED DESCRIPTION

The (-) enantiomer of tenatoprazole, or (-) tenatoprazole, corresponds to (-)-5-methoxy-2-[[(4-methoxy-3,5-dimethyl-2-pyridyl)methyl]sulfinyl]imidazo[4,5-b]pyridine. It can be represented by the following general formula:

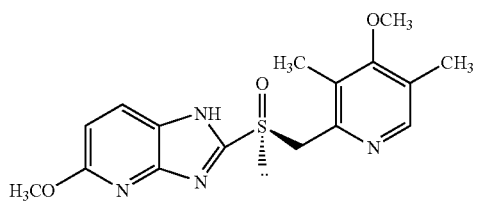

According to a preferred method of preparation, the (−) enantiomer of tenatoprazole can be obtained in an enantioselective manner under good purity and yield conditions, by enantioselective oxidation of the corresponding sulphide in the presence of a specific vanadium-based catalyst. Such method is described in French patent application 0303914.

The sulphide used as starting material is a known product that can be prepared according to several methods described in literature, and for example, according to the methods described in Patents No. EP 254.588 and EP 103.553.

The oxidizing agent used in the method of the invention is preferably a peroxide, for example hydrogen peroxide. According to an advantageous method of implementation, highly concentrated hydrogen peroxide, higher than 30% for example, is used.

According to the invention, the catalyst can be selected from V oxo-vanadium complex catalysts, such as vanadium acetylacetonate. Such catalysts are commercially available.

A ligand such as a Schiff base derived from a substituted salicylic aldehyde and from a chiral amino-alcohol, is preferably used in combination with the catalyst. A most preferred ligand is 2,4-di-tert-butyl-6-[1-S-hydroxymethyl-2-methyl-propylimino)-methyl]-phenol. Under operating conditions, the ligand and the metallic catalyst form an asymmetric complex where the metal is oxidized by the oxidizing agent.

The reaction may be carried out in a solvent, in a neutral or weakly basic medium, for example in methanol, tetrahydrofuran, methylene chloride, acetonitrile or toluene. The base used otherwise may be a tertiary amine such as pyridine, di-isopropylethylamine or triethyl-amine. The oxidation reaction is easily conducted at low temperatures or at room temperature.

The (−) enantiomer of tenatoprazole can be easily obtained in a pure optical form according to the above method of synthesis.

Here, "pure optical form" means that the (−) enantiomer is substantially free of the (+) enantiomer, or contains only traces of it. If relevant, salification with a base is then performed in an appropriate solvent to form a salt, and particularly an alkaline or earth-alkaline metal salt.

This form can be measured by optical rotation measurements using standard techniques.

For example, it is possible to prepare a solution of the desired enantiomer at 0.25% (50 mg of a sample per 20 ml of solvent) dissolved in dimethylformamide or acetonitrile, and using a polarimeter of a commonly employed type (e.g., Jobin Yvon). In dimethylformamide and acetonitrile, the angle of optical rotation of (−) tenatoprazole is levorotatory, and its melting point is 127-130° C. (decomposition).

The (−) enantiomer of tenatoprazole can also be obtained in a pure optical form by well known techniques, using any appropriate method of separation, for example by preparative column chromatography, such as chiral chromatography or high performance liquid chromatography (HPLC).

The principle of the chiral chromatography method is based on the difference in affinity existing between (+) and (−) enantiomers and the chiral selector of the stationary phase. This method enables the separation of the enantiomers with a satisfactory yield. If necessary, the racemic mixture of tenatoprazole can be obtained using known processes, for example according to the method described in Patent No. EP 254.588. Thus, it can be prepared using an oxidizing agent, such as perbenzoic acid, to treat the corresponding sulphide arising from the condensation of a thiol and a pyridine, preferably in the presence of a base such as potassium hydroxide in an appropriate solvent, for example ethanol, under heating.

The known method used to separate the enantiomers of tenatoprazole can provide the isolation of the (−) enantiomer with excellent purity (chiral purity: minimum 98.8% of the surface area).

In the studies conducted by the applicant, it was confirmed that the (−) isomer of tenatoprazole obtained according to the method described in the present invention has the "S" configuration, which means that the (+) isomer has the "R" configuration.

Pharmacological Studies

In vivo Studies in Rats: Assessment of Volume and pH of Gastric Secretion.

Studies conducted by the applicant in vivo in a model of ligature of the pylorus in the rat have investigated the pharmacological effects of the (−) and (+) isomers of tenatoprazole. In this well established and validated model, animals are pre-treated at different time points (10, 16 and 20 h) before ligature of the pylorus, and the volume and pH of the gastric secretions are measured 4 h after the ligature.

Significant differences between the two isomers can be observed with this model, as summarized in the following table. Indeed, 10 h after treatment administration the (−) isomer remains pharmacologically active. It increases the pH by 49% (p<0.01) and decreases gastric acidity by about 55% (p<0.01), as compared to the control group, whereas the effect of the (+) isomer is no longer significant.

|  | pH | Free acid |
|---|---|---|
| (−) isomer | +49% | −55% |
| (+) isomer | +30% | −30% |

In vivo Studies in Dogs: Assessment of the Antisecretory Effect.

Studies conducted by the applicant in vivo in dogs have investigated the antisecretory effect of the (−) isomer of tenatoprazole and the (+) isomer, by measuring the intragastric pH after treatment administration for 6 days (10 mg/kg/day). The profile of intragastric pH during a 24-hour period was recorded on the first two days of administration, on the 6th day, and two days after treatment termination. These pH values were compared to those measured at baseline, prior to treatment administration.

It was demonstrated that the (−) isomer of tenatoprazole and the (+) isomer of tenatoprazole inhibit gastric secretion in dogs. However a significant effect can be only observed with the (−) isomer of tenatoprazole from the first day of administration, and is maintained until two days after treatment termination.

The results corresponding to the pH>3 and pH>4 holding time for 24 h, expressed in percent, are described below:

|  | % of holding time for 24 hours | |
|---|---|---|
|  | pH > 3 | pH > 4 |
| basal | 21 | 9 |
| 1st day of treatment | 73 | 55 |
| 2nd day of treatment | 82 | 75 |
| 6th day of treatment | 93 | 75 |

In vivo Studies in Rats: Assessment of the Onset of Healing and the Increase of Normalisation of Histological Changes of the Lesions.

Other in vivo experiments conducted by applicant in rats have demonstrated that the onset of healing of ulcerative lesions was significantly improved with the administration of the (−) enantiomer of tenatoprazole, as compared with the effects obtained with the (+) enantiomer. Thus, the effect observed with the (−) enantiomer of tenatoprazole appeared 1 day before those of the (+) enantiomer. Such unexpected difference was also followed by a significant increase in the quality of such healing due to the increase in the normalization of histological changes when the (−) enantiomer was administered. These changes consisted in a reduction of the ultrastructural damage resulting in a complete morphological recovery of the oesophageal epithelium.

Such pharmacological effect of the (−) enantiomer on both qualitative and quantitative improvement will result in a significant decrease in the number of relapses of oesophagitis.

Pharmacokinetic Studies

Studies performed by the applicant on the (−) enantiomer of tenatoprazole prepared as above have unexpectedly demonstrated that it possesses pharmacokinetic properties which are fundamentally different from those of the other PPIs or the (+) enantiomer, thus suggesting that the (−) enantiomer could be used in specific therapeutic indications.

Thus, the (−) enantiomer of tenatoprazole is significantly different in terms of pharmacokinetic properties, as shown by the studies described herein. This characteristic is essential, as it will provide the clinician with a medicinal product adequate for an effective treatment of specific diseases and conditions.

More particularly, the unexpected pharmacokinetic properties of the (−) enantiomer of tenatoprazole were discovered during an extensive program of pharmacokinetic and metabolism studies in vitro and in vivo. Because of a variability observed in pharmacokinetics, and notably in the $AUC_{0-inf}$ (area under the curve) and $t_{1/2}$ (elimination half-life), the genotype of some subjects of the study was assessed in order to identify which type of metaboliser (i.e., slow or rapid) they belonged to.

It must be pointed out that an important aspect of the metabolism of PPIs is that they are mostly metabolised by the cytochrome CYP2C19 whose gene is located on chromosome 10. Therefore, the PPIs exhibit a "genetic polymorphism", that is, an activity which varies as a function of the genotype of a patient. This results in variable plasma levels of the drug and a susceptibility to potentially harmful drug interactions, depending on the individual concerned.

In vitro Pharmacokinetic and Metabolism Studies

Indeed, in vitro studies conducted on the cytochromes that metabolise tenatoprazole have revealed the existence of a significant difference in the metabolism of the (−) versus the (+) isomers, as shown in the following table:

|  | Vmax (−) | Vmax (+) |
|---|---|---|
| CYP2C19 | 1.90 | 12.63 |

In the above table, the value Vmax is the maximal rate of metabolism (Vmax) measured as pmol/min per pmol of cytochrome. Vmax (−) is the value of Vmax of the (−) enantiomer of tenatoprazole.

From these results it can be concluded that the (−) enantiomer is metabolised approximately 7 times more slowly than the (+) enantiomer. Consequently, it can be anticipated that the (−) enantiomer of tenatoprazole will have a much longer mean residence time (MRT) in the human body, by comparison with the (+) enantiomer.

Further, it has been shown that different cytochromes intervene in the metabolism of tenatoprazole.

The (−) enantiomer is mainly metabolised via the cytochrome CYP3A4, which can compensate for a potential deficiency or blockade of cytochrome CYP2C 19. The (+) enantiomer is metabolised via two pathways, i.e. mainly the CYP2C19 and, to a lesser extent, by CYP3A4.

In addition, it has become clear that subjects homozygous for a mutation which gives rise to the CYP2C19*2/*2 genotype exhibit pharmacokinetic characteristics of tenatoprazole totally different from those seen in the general population. The homozygous subjects have a very weak metabolic activity of the cytochrome CYP2C19 which is responsible for the metabolism of tenatoprazole. The analysis of plasma has shown that these subjects display a highly significant increase in the (+) enantiomer when compared with the (−) enantiomer. These subjects are qualified as "slow metabolisers".

Conversely, subjects who are characterised by the CYP2C19*1/*1 genotype are "rapid metabolisers" and display a concentration of (−) enantiomer higher than that of the (+) enantiomer, as summarised in the following table:

| Genotype | Metabolic activity | (−) Enantiomer | (+) Enantiomer |
|---|---|---|---|
| CYP2C19*2/*2 | Weak activity of cytochrome CYP2C19 = "Slow metabolisers" |  | Increased |
| CYP2C19*1/*1 | Normal activity of cytochrome CYP2C19 = "Rapid metabolisers" | Increased |  |

Taking into account the possible saturation of CYP2C19, it is anticipated that the potential risk of drugs interactions in patients receiving concomitant medications will be dramatically decreased when the (−) enantiomer will be administered.

In vivo Pharmacokinetic and Metabolism Studies

Other studies performed by applicant in dogs have shown that the administration of the (−) enantiomer of tenatoprazole resulted in a difference of rate of metabolism leading to a significantly longer half-life for the (−) enantiomer of tenatoprazole in comparison with the (+) enantiomer.

Clinical Studies

In order to assess the difference in pharmacokinetic characteristics between the (−) enantiomer of the invention and the (+) enantiomer, a pharamacokinetic study was conducted.

Said study was carried out in Caucasian subjects, after an acute and repeated administration (7 days) of tenatoprazole. After the 7 days of treatment, it was observed that the plasma concentration of the (−) isomer is linear with the dose, as is the case for its AUC which is correlated with the intra-gastric pH of the subject and thus of the activity of the treatment. In contrast, it was observed that the evolution of the plasma concentration of the (+) isomer is not linear, and thus not predictive of the efficacy and the tolerability of the drug. Furthermore, it was observed that the between-subject variability of pharmacokinetic parameters is markedly lower for the (−) isomer compared to the (+) isomer.

In another study, it was assessed that the elimination half-life of the (−) isomer of tenatoprazole is approximately 4 times shorter than that of the (+) isomer in slow metabolisers (which are deficient in CYP2C 19 activity), as summarised in the following table:

| Slow metabolisers: | T1/2 (hours): |
|---|---|
| (−) isomer | 9.7 ± 0.9 |
| (+) isomer | 36.7 ± 4.5 |

Thus, the results of the above confirm that the (−) enantiomer of tenatoprazole possesses a much better predictability of action, which would make it possible to anticipate and limit the potential risks of drug interactions in patients receiving concomitant medications.

Thus, the overall conclusion of the above study is that the (−) enantiomer of tenatoprazole possesses a superior efficacy and a significant safety profile, which will prevent from serious adverse drug reactions.

All these unexpected results have led to the proposal of isolating and administering only one enantiomer of tenatoprazole, the (−) enantiomer, which has the following advantages:

A reduction in between-subject variations, hence a better use of the product and a more homogenous response to treatment in all patients;

An improved tissue exposure of the product, because its rate of metabolism is slower and the mean residence time (MRT) in the body is longer;

A reduction in the number of potential interactions with concomitant medications. Indeed, the (−) isomer is metobolized through two ways, i.e. the 2C19 and 3A4 cytochromes, which compensates for a possible deficiency or blocking of 2C19 cytochrome.

An ease of use in all types of patients, whether they are slow or rapid metabolisers. Indeed, the (−) enantiomer in a slow metaboliser would be metabolised by cytochrome CYP3A4, thus making it possible to achieve uniform pharmacokinetic parameters independently of the genotype of the patients.

an improved efficacy/safety profile in all types of patients to treat digestive diseases and conditions such as typical and oesophagal symptoms of gastro-oesophagal reflux, digestive bleeding and dyspepsia.

an improved onset of healing as well as an increase in the normalization of histological changes of gastric lesions.

Furthermore, the isolation of the (−) enantiomer of tenatoprazole has made it possible to determine its pharmacokinetic profile and notably a mean plasma half-life of approximately 10 to 12 hours at doses of between 10 mg and 80 mg. In contrast, previous studies have shown that the racemic mixture has a mean plasma half-life of approximately 7 hours at this range of doses The unexpected properties of the (−) enantiomer of tenatoprazole, and more particularly its specific pharmacokinetic and metabolism parameters, indicate that the (−) enantiomer of tenatoprazole can be advantageously used for the treatment of digestive diseases and conditions where it is necessary to obtain an effective and prolonged inhibition of acid secretion. This would be the case in patients with Barrett's syndrome, which causes pre-cancerous damage linked to gastro-oesophageal reflux, and where the risk of oesophageal adenocarcinoma is directly proportional to the incidence, severity and duration of the episodes of gastro-oesophageal reflux.

The (−) enantiomer of tenatoprazole is also suitable for the treatment of patients with the Zollinger-Ellison syndrome and other syndromes involving acid hypersecretion, and for the treatment of atypical and oesophageal symptoms of gastro-oesophageal reflux, digestive bleeding refractory to other PPIs, and especially suitable for treatment of patients receiving multiple drug therapy, and especially elderly patients, with the aim of preventing adverse events associated with drug interactions.

The (−) enantiomer of tenatoprazole can also be used, preferably in combination with one or more antibiotics, to treat ulcers in the event of *Helicobacter pylori* infection, and notably to help eradicate *Helicobacter pylori* by facilitating the healing of the ulcer and prevent recurrence.

For the treatment of the conditions listed above, and most particularly the Barrett and Zollinger-Ellison syndromes, and of gastro-oesophageal reflux and digestive bleeding, the (−) enantiomer of tenatoprazole can be administered in standard forms adapted to the method of administration chosen, for example via the oral or parenteral routes, and preferably via the oral or intravenous routes.

For example, it is possible to use tablet or capsule formulations containing the (−) enantiomer of tenatoprazole as the active substance, or oral solutions or emulsions or solutions for parenteral administration containing a tenatoprazole salt with a standard, pharmaceutically-acceptable substrate. The salt of the (−) enantiomer of tenatoprazole can be chosen, for example, from amongst sodium, potassium, lithium, magnesium or calcium salts.

An example of an appropriate formulation for tablets containing 30 mg of the (−) isomer of tenatoprazole in combination with pharmaceutically acceptable substrates and excipients, including at least one excipient giving gastro-resistant properties to the formulation, is shown below:

| | |
|---|---|
| (−) tenatoprazole | 30.0 mg |
| lactose | 40.0 mg |
| aluminum hydroxide | 17.5 mg |
| hydroxypropyl cellulose | 8.0 mg |
| talc | 4.5 mg |
| titanium dioxide | 5.0 mg |
| magnesium stearate | 2.0 mg |
| standard excipients | qs 160.0 mg |

An example of a formulation for a size-2, gastro-resistant enteric capsule (capsule shell made of acetophtalate, polyvinylpyrrolidone derivatives and acrylic resins), containing 40 mg of the (−) isomer of tenatoprazole is shown below:

| | |
|---|---|
| (−) tenatoprazole | 40.0 mg |
| lactose | 200.0 mg |
| magnesium stearate | 10.0 mg |

The dosage is determined by the practitioner as a function of the patient's state and the severity of the condition. It is generally between 10 and 120 mg per day, and preferably between 10 and 80 mg per day of the (−) enantiomer of tenatoprazole. For example, it can be administered at a rate of one daily intake of 1 or 2 unit doses (e.g., tablets), each containing 10 to 80 mg and preferably 15 or 20 to 40 or 60 mg of the active substance, for a period of time which can range from 4 to 12 weeks in the context of an initial or maintenance therapy. In the case of a paediatric form adapted for use in young children, for example in the form of an oral solution, the unit dose can be lower, for example 2 or 5 mg. In the case of severe disorders, it may be effective to administer the medicinal product in the first instance via the intravenous route, and subsequently via the oral route. The invention also has the advantage of permitting effective, sequential treatment with the weekly administration of a single tablet containing 60 to 90 mg.

One of the advantages of the present invention is that it allows treatment of the diseases and conditions referred to above, including the treatment of ulcers resulting from *Helicobacter pylori* infection, with a dosage limited to a single dose of medication per day, unlike other standard drugs, including standard PPIs, which require two daily doses.

In order to illustrate the present invention, an example of preparation of the (−) enantiomer of tenatoprazole is described below.

EXAMPLE

3 L of methylene chloride and then 360 g of 5-methoxy-2-[[4-methoxy-3,5-dimethyl-2-pyridyl)methyl]thio]imidazo[4,5-b]pyridine are added in a 5 L flask. The mixture is left under stirring for 30 minutes at room temperature.

700 mL of acetonitrile, 5.22 g of 2,4-di-tert-butyl-6-[1-R-hydroxymethyl-2-methyl-propylimino)-methyl]-phenol, and 2.90 g of vanadyl acetylacetonate are dropped one after the other in a 2 L flask. The mixture is kept under stirring at room temperature. After an stirring for 30 min, such solution is added to the preceding one.

135 mL of hydrogen peroxide at 30% are added to this mixture under stirring for 20 hours at room temperature. After separation of the aqueous phase, the organic phase is washed twice with water, then dried and concentrated under reduced pressure. 283 g of the desired enantiomer are obtained, with an enantiomeric excess higher than 80% (75% yield). Two successive recrystallisations are performed in a methanol/water of DMF/ethyl acetate mixture and the enantiomer is obtained with an enantiomeric excess higher than 99%.

F: 127.5° C.

$[\alpha]_D$: −186.6 (DMF)

UV spectrum (methyl alcohol-water): $\lambda_{max}$: 272 nm, 315 nm.

Infra-red (KBr): 3006, 1581, 1436, 1364, 1262 cm$^{-1}$.

NMR $^{13}$C (KOH, reference: sodium 3-(trimethylsilyl)-1-propanesulfonate) δ (ppm): 13.2; 15.0; 56.6; 60.8; 62.6; 107.2; 129.5; 130.4; 131.9; 135.1; 150.5; 151.4; 156.9; 160.7 163.0; 166.6.

NMR $^1$H (DMSO d$_6$, reference: TMS) δ (ppm): 2.20 (s, 6H), 3.70 (s, 3H), 3.91 (s, 3H), 4.69-4.85 (m, 2H), 6.80 (d, J 8.5 Hz, 1H), 7.99 (d, J 8.5 Hz, 1 H), 8.16 (s, H), 13.92 (s, 1H).

The invention claimed is:

1. A pharmaceutical composition comprising (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer, one or more antibiotics, and one or more pharmaceutically acceptable excipients or substrates.

2. A method of treatment of digestive diseases and conditions comprising administering to a subject in need thereof an effective amount of (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer.

3. A method of treatment according to claim 2, wherein the digestive diseases and conditions are selected from the group consisting of Barrett's syndrome, Zollinger-Ellison syndrome, atypical and oesophageal symptoms of gastro-oesophageal reflux, and digestive bleeding refractory to other proton pump inhibitors (PPIs).

4. A method of treatment of digestive diseases and conditions comprising administering to a subject in need thereof an effective amount of a pharmaceutical composition comprising (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer, and one or more pharmaceutically acceptable excipients or substrates.

5. A method of treatment according to claim 4, wherein the digestive diseases and conditions are selected from the group consisting of Barrett's syndrome, Zollinger-Ellison syndrome, atypical and oesophageal symptoms of gastro-oesophageal reflux, and digestive bleeding refractory to other proton pump inhibitors (PPIs).

6. A method of treatment according to claim 2, wherein the effective amount of (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer, exhibits improved pharmacokinetic properties.

7. A method of treatment according to claim 2, wherein the (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer is administered orally.

8. A method of treatment according to claim 2, wherein the (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer is administered via a parenteral solution.

9. A combination therapy for the treatment of digestive disease and conditions comprising a pharmaceutically effective amount of (−)-5-methoxy-2-[[4-methoxy-3,4-dimethyl-2-pyridyl)methyl]sulfinyl]imidazol[4,5-b]pyridine or a pharmaceutically acceptable salt thereof, substantially free of the (+) enantiomer, and a second agent selected from the group consisting of a proton pump inhibitor (PPI).

10. A combination therapy according to claim 9, wherein the proton pump inhibitor (PPI) is selected from the group consisting of omeprazole, rabeprazole, pantoprazole, and lansoprazole.

* * * * *